United States Patent
Suetterlin et al.

(10) Patent No.: US 10,988,565 B2
(45) Date of Patent: *Apr. 27, 2021

(54) PROCESS FOR PRODUCING ELASTIC AND TEAR-RESISTANT POLYURETHANE FOAMS AND USES

(71) Applicant: Covestro Deutschland AG, Leverkusen (DE)

(72) Inventors: Jan Suetterlin, Cologne (DE); Marc-Stephan Weiser, Kürten-Dürscheid (DE); Sascha Plug, Leverkusen (DE); Sebastian Dörr, Düsseldorf (DE); Claudine Stoye, Cologne (DE)

(73) Assignee: Covestro Deutschland AG, Leverkusen (DE)

( * ) Notice: Subject to any disclaimer, the term of this patent is extended or adjusted under 35 U.S.C. 154(b) by 106 days.

This patent is subject to a terminal disclaimer.

(21) Appl. No.: 16/245,470

(22) Filed: Jan. 11, 2019

(65) Prior Publication Data

US 2019/0218330 A1  Jul. 18, 2019

(30) Foreign Application Priority Data

Jan. 12, 2018 (EP) ................................. 18151353

(51) Int. Cl.

| | |
|---|---|
| C08G 18/10 | (2006.01) |
| C08G 18/48 | (2006.01) |
| C08G 18/72 | (2006.01) |
| C08G 18/79 | (2006.01) |
| C08G 18/08 | (2006.01) |
| C08G 18/73 | (2006.01) |
| A61F 13/00 | (2006.01) |
| A61L 15/26 | (2006.01) |
| A61L 15/42 | (2006.01) |
| C08G 101/00 | (2006.01) |

(52) U.S. Cl.
CPC ............ *C08G 18/10* (2013.01); *C08G 18/14* (2013.01); *C08G 18/485* (2013.01); *C08G 18/4833* (2013.01); *C08G 18/722* (2013.01); *C08G 18/73* (2013.01); *C08G 18/792* (2013.01); *A61F 2013/0074* (2013.01); *A61L 15/26* (2013.01); *A61L 15/425* (2013.01); *C08G 2101/0008* (2013.01); *C08G 2101/0058* (2013.01); *C08G 2101/0066* (2013.01); *C08G 2101/0083* (2013.01)

(58) Field of Classification Search
CPC ............ A61F 2013/0074; A61L 15/26; A61L 15/425; C08G 18/10; C08G 18/14; C08G 18/4833; C08G 18/485; C08G 18/722; C08G 18/73; C08G 18/792

See application file for complete search history.

(56) References Cited

U.S. PATENT DOCUMENTS

| | | |
|---|---|---|
| 3,903,232 A | 9/1975 | Wood et al. |
| 4,137,200 A | 1/1979 | Wood et al. |
| 5,104,909 A | 4/1992 | Grasel et al. |
| 5,849,850 A | 12/1998 | Bleys et al. |
| 8,980,966 B2 | 3/2015 | Dörr et al. |
| 9,228,049 B2 | 1/2016 | Dörr et al. |

(Continued)

FOREIGN PATENT DOCUMENTS

| | | |
|---|---|---|
| EP | 2143744 A1 | 1/2010 |
| EP | 2470580 A2 | 7/2012 |

(Continued)

*Primary Examiner* — John M Cooney

(74) *Attorney, Agent, or Firm* — Faegre Drinker Biddle & Reath LLP

(57) ABSTRACT

The invention provides a process for producing polyurethane foams, in which compositions comprising
- A) isocyanate-functional prepolymers obtainable by the reaction of
  - A1) low molecular weight diisocyanates of molar mass from 140 to 278 g/mol with
  - A2) polyalkylene oxides having an OH functionality of two or more,
  - A3) optionally further isocyanate-reactive components not covered by A2),
- B) water in an amount of at least 2% by weight, based on the total weight of the composition;
- C) optionally heterocyclic 4-membered or 6-membered ring oligomers of low molecular weight diisocyanates having a molar mass of 140 to 278 g/mol;
- D) optionally catalysts;
- E) optionally salts of weak acids, the corresponding free acids of which have a pKA in water at 25° C. of ≥3.0 and ≤14.0;
- F) optionally surfactants;
- G) optionally mono- or polyhydric alcohols or polyols, and
- H) optionally hydrophilic polyisocyanates obtainable by reaction of
  - H1) low molecular weight diisocyanates of molar mass from 140 to 278 g/mol and/or polyisocyanates preparable therefrom and having an isocyanate functionality of 2 to 6 with
  - H2) monofunctional polyalkylene oxides of OH number from 10 to 250 and of ethylene oxide content from 50 to 100 mol %, based on the total amount of the oxyalkylene groups present, are provided, foamed and cured, wherein the isocyanate-containing components, especially components A, C and H, have a total isocyanate content within a range from 2% to 8% by weight and a content of urethane groups of 1.0 to 3.5 mol/kg, based in each case on the total amount of the isocyanate-containing components, and also the foams thus produced and the uses thereof.

13 Claims, No Drawings

(56) References Cited

U.S. PATENT DOCUMENTS

| | | | |
|---|---|---|---|
| 9,364,577 | B2 | 6/2016 | Niesten et al. |
| 9,458,300 | B2 * | 10/2016 | Dorr et al. |
| 2006/0142529 | A1 | 6/2006 | Thiede et al. |
| 2011/0184080 | A1 | 7/2011 | Schönberger et al. |
| 2012/0289622 | A1 * | 11/2012 | Niesten et al. |
| 2013/0131207 | A1 * | 5/2013 | Niesten et al. |
| 2013/0136785 | A1 * | 5/2013 | Schonberger et al. |

FOREIGN PATENT DOCUMENTS

| | | | |
|---|---|---|---|
| EP | 2585505 | A1 | 5/2013 |
| EP | 2632501 | A1 | 9/2013 |
| EP | 17156493.3 | | 2/2017 |
| EP | 3235520 | A1 | 10/2017 |
| WO | WO-2011006608 | A1 | 1/2011 |
| WO | WO-2011023762 | A2 | 3/2011 |
| WO | WO-2011161048 | A1 | 12/2011 |
| WO | WO-2012055834 | A1 | 5/2012 |
| WO | WO-2018149835 | A1 | 8/2018 |

* cited by examiner

PROCESS FOR PRODUCING ELASTIC AND TEAR-RESISTANT POLYURETHANE FOAMS AND USES

CROSS-REFERENCE TO RELATED APPLICATIONS

This application claims priority to European Application No. 18151353.2, filed Jan. 12, 2018, which is incorporated herein by reference in its entirety.

The invention provides a process for producing polyurethane foams, in which compositions comprising isocyanate-functional prepolymers A), water B), optionally heterocyclic 4-membered or 6-membered ring oligomers of low molecular weight diisocyanates having a molar mass of 140 to 278 g/mol C), optionally catalysts d), optionally salts of weak acids, the corresponding free acids of which have a pKA in water at 25° C. of ≥3.0 and ≤14.0 E), optionally surfactants F), optionally mono- or polyhydric alcohols or polyols G), optionally hydrophilic polyisocyanates H), wherein the isocyanate-containing components, especially components A), C) and H), have a total isocyanate content within a range from 2% to 8% by weight and a content of urethane groups of 1.0 to 3.5 mol/kg, based in each case on the total amount of the isocyanate-containing components A), C) and H); and also the foams thus produced and the uses thereof.

BACKGROUND OF THE INVENTION

There are known processes in the prior art by which foams can be produced by mixing polyisocyanate-containing starting materials together with water. More particularly, patent applications EP2143744, EP2470580, EP2585505 and EP2632501 describe such processes using prepolymer formulations with aliphatic isocyanates that have an isocyanate content within a range from 2% to 8% by weight. In all the examples described, exclusively a urethane content of less than 1.0 mol/kg is used. The NCO/OH ratio during the prepolymer synthesis in the examples has a value of 15. None of the abovementioned documents describes mechanical properties of the foams produced.

In addition, foams based on aromatic polyisocyanates are known. For instance, in patent applications U.S. Pat. Nos. 3,903,232, 4,137,200, 5,849,850 and US2006142529, prepolymer formulations having either isocyanate contents >8% by weight or urethane contents <1.0 mol/kg are used.

An aim that has not been achieved to date in the production of such foams, especially in the use thereof in medical applications, is to co-optimize various properties, such as the flexibility of the foam, the amount of liquids absorbed, tear strength and a foam density that is not too high. However, only in this way would it be possible to provide a foam that has maximum tear strength but is nevertheless flexible and at the same time has high absorption for liquids with minimum weight. Especially in order to be able to use such a foam for wound-dressing foams for example, the optimization of all the properties mentioned would be desirable. However, it has been found to date that a foam having high absorption capacity for aqueous media (also called liquid absorption hereinafter) has comparatively low flexibility or breaking strength. There is therefore a need to provide foams having a combination of optimized properties.

BRIEF SUMMARY OF THE INVENTION

One problem addressed by the present invention was that of at least partly overcoming at least one disadvantage of the prior art.

A further problem addressed by the present invention was that of providing a foam or a process for producing said foam, such that the foam, with good absorption of liquids, still has high flexibility, i.e. easy deformability, and high breaking strength in order to have maximum durability and nevertheless be flexible. More particularly, the foam should have an F20 value of ≤50 kPa, or preferably ≤30 kPa. The F20 corresponds to the tension at 20% elongation in the stress/strain test according to DIN EN ISO 527-2, as set out in detail under Methods.

In addition, a problem addressed by the present invention was that of providing a foam or a process for producing said foam, such that the foam has a quotient of breaking strength to F20 of at least 3.5, preferably of at least 4.0, preferably of at least 5.0 or preferably of at least 7.5, and at the same time still has high flexibility. More particularly, this foam should not exceed a density of 300 g/l, or preferably of 200 g/l.

A further problem addressed by the present invention was that of providing a foam or a process for producing said foam that enables production of a foam in the form of foam strips that can be rolled up without tearing of the foam strips under the tensile forces that occur when they are rolled up. The foams should preferably have a breaking strength of ≥50 kPa, or preferably ≥100 kPa.

In addition, a problem addressed was that of providing a foam and a process for producing said foam, in which the foam has a high liquid absorption, preferably within a range from 530% to 4000%, or preferably from 800% to 3500%, more preferably from 1000% to 3000%, based on the original liquid content. At the same time, the foam should have pleasant tactile properties and be able to adapt readily to curved surfaces.

DETAILED DESCRIPTION OF THE INVENTION

It has been found that, surprisingly, the combination of features of the subject-matter of Claim 1 was able to solve at least one of the problems.

The invention firstly relates to a process for producing polyurethane foams, in which compositions comprising A) isocyanate-functional prepolymers obtainable by the reaction of
 A1) low molecular weight diisocyanates of molar mass from 140 to 278 g/mol with
 A2) polyalkylene oxides having an OH functionality of two or more, preferably within a range from 2 to 6, preferably within a range from 2 to 5, or preferably 2 to 4,
 A3) optionally further isocyanate-reactive components not covered by A2);
B) water in an amount of at least 2% by weight, preferably of at least 5% by weight, or preferably of at least 10% by weight, or preferably within a range from 2% to 40% by weight, or preferably within a range from 5% to 30% by weight, or preferably within a range from 10% to 25% by weight, based on the total weight of the composition;
C) optionally heterocyclic 4-membered or 6-membered ring oligomers of low molecular weight diisocyanates having a molar mass of 140 to 278 g/mol;
D) optionally catalysts;
E) optionally salts of weak acids, the corresponding free acids of which have a pKA in water at 25° C. of ≥3.0 and ≤14.0;
F) optionally surfactants; and
G) optionally mono- or polyhydric alcohols or polyols;

H) optionally hydrophilic polyisocyanates obtainable by reaction of
   H1) low molecular weight diisocyanates of molar mass from 140 to 278 g/mol and/or polyisocyanates preparable therefrom and having an isocyanate functionality of 2 to 6 with
   H2) monofunctional polyalkylene oxides of OH number from 10 to 250 and of ethylene oxide content from 50 to 100 mol %, based on the total amount of the oxyalkylene groups present,
are provided, foamed and cured,
wherein the isocyanate-containing components, especially components A, C and H, have a total isocyanate content within a range from 2% to 8% by weight and a content of urethane groups of 1.0 to 3.5 mol/kg, based in each case on the total amount of the isocyanate-containing components. Preferably, the isocyanate-containing components, especially components A, C and H, have a total isocyanate content within a range from 3% to 7% or preferably within a range from 4% to 6.5% by weight, and preferably a content of urethane groups within a range from 1.5 to 3.0 mol/kg, or preferably within a range from 1.7 to 2.8 mol/kg, based in each case on the total amount of the isocyanate-containing components.

Preferably, the prepolymers A) used have a residual monomer content of below 0.5% by weight based on the prepolymer. This content can be achieved via appropriately chosen use amounts of the diisocyanates A1) and the polyalkylene oxides A2). However, preference is given to the use of the diisocyanate A1) in excess and with subsequent, preferably distillative, removal of unconverted monomers.

In the preparation of the isocyanate-functional prepolymers A), the ratio of the polyalkylene oxides A2) to the low molecular weight, aliphatic diisocyanates A1) is typically adjusted such that, for every 1 mol of OH groups of the polyalkylene oxides A2), there are 1.1 to 20 mol, preferably 1.3 to 5 mol and more preferably 1.5 to 3.5 mol NCO groups of the low molecular weight, aliphatic diisocyanate A1).

The reaction can be effected in the presence of urethanization catalysts such as tin compounds, zinc compounds, amines, guanidines or amidines, or in the presence of allophanatization catalysts such as zinc compounds.

The reaction is typically effected at 25° C. to 140° C., preferably 60° C. to 100° C.

If excess isocyanate has been employed, the excess of low molecular weight, aliphatic diisocyanate is then removed, preferably by thin-film distillation.

Before, during and after the reaction or the distillative removal of the excess diisocyanate, preference is given to adding acidic or alkylating stabilizers, such as benzoyl chloride, isophthaloyl chloride, methyl tosylate, chloropropionic acid, HCl, dibutyl phosphate or antioxidants such as di-tert-butylcresol or tocopherol.

The NCO content of the isocyanate-functional prepolymers A) is preferably 1.5% to 8% by weight, more preferably 2% to 7.5% by weight and most preferably 3% to 7% by weight.

Examples of low molecular weight, aliphatic diisocyanates of component A1) are hexamethylene diisocyanate (HDI), isophorone diisocyanate (IPDI), butylene diisocyanate (BDI), pentamethylene diisocyanate (PDI), bisisocyanatocyclohexylmethane (HMDI), 2,2,4-trimethylhexamethylene diisocyanate, bisisocyanatomethylcyclohexane, bisisocyanatomethyltricyclodecane, xylene diisocyanate, tetramethylxylylene diisocyanate, norbornane diisocyanate, cyclohexane diisocyanate or diisocyanatododecane, preference being given to hexamethylene diisocyanate (HDI), isophorone diisocyanate (IPDI), butylene diisocyanate (BDI), pentamethylene diisocyanate (PDI), and bis(isocyanatocyclohexyl)methane (HMDI). Particular preference is given to PDI, HDI, IPDI, very particular preference to hexamethylene diisocyanate and pentamethylene diisocyanate.

If aromatic diisocyanates are used as component A1, these are preferably toluene 2,4-diisocyanate (2,4-TDI), toluene 2,6-diisocyanate (2,6-TDI) or methylene diphenyl 2,2'-diisocyanate (2,2'-MDI), methylene diphenyl 2,2'-diisocyanate (2,4'-MDI), methylene diphenyl 4,4'-diisocyanate (4,4'-MDI), or mixtures of at least two of these.

Polyalkylene oxides of component A2) may be any polyalkylene oxides that the person skilled in the art would use for the purpose. Examples of these are selected from the group consisting of polyethylene oxide, polypropylene oxide, polytetrahydrofuran or a mixture of at least two of these. Polyalkylene oxides of component A2) are preferably copolymers of ethylene oxide and propylene oxide having an ethylene oxide content, based on the total amount of the oxyalkylene groups present, of 50 to 100 mol %, preferably 60 to 90 mol %, started from polyols or amines Preferred starters of this kind are selected from the group consisting of ethylene glycol, propane-1,3-diol, butane-1,4-diol, glycerol, trimethylolpropane (TMP), sorbitol, pentaerythritol, triethanolamine, ammonia and ethylenediamine, or a mixture of at least two of these.

The polyalkylene oxides of component A2) typically have number-average molecular weights of 250 to 10 000 g/mol, preferably of 300 to 2800 g/mol, or preferably 350 to 1500 g/mol.

In addition, the polyalkylene oxides of component A2) have OH functionalities of 2 to 6, preferably of 2 to 5, more preferably of 2 to 4.

For component A3), in principle, preference is given to using any of the mono- and polyhydric alcohols or mono- and polyfunctional amines that are known per se to the person skilled in the art, and mixtures thereof. These are mono- or polyhydric alcohols or polyols, such as ethanol, propanol, butanol, decanol, tridecanol, hexadecanol, ethylene glycol, neopentyl glycol, butanediol, hexanediol, decanediol, trimethylolpropane, glycerol, pentaerythritol, monofunctional polyether alcohols and polyester alcohols, polyetherdiols and polyesterdiols or mixtures of at least two of these. Examples of mono- or polyfunctional amines include butylamine, ethylenediamine or amine-terminated polyalkylene glycols (e.g. Jeffamine®).

In the preparation of the prepolymer A), it is possible to use catalysts as described for component D) for example.

The water for use as component B) can be used as such, as water of crystallization in a salt, as a solution in a dipolar-aprotic solvent or else as an emulsion. Preference is given to using the water as such or in a dipolar-aprotic solvent. Very particular preference is given to using the water as such.

Any compounds of component C) that are to be used are heterocyclic 4-membered or 6-membered ring oligomers of low molecular weight diisocyanates having a molar mass of 140 to 278 g/mol, such as isocyanurates, iminooxadiazinediones or uretdiones of the aforementioned low molecular weight diisocyanates. Aliphatic diisocyanates are preferably used for component C). Preference is given to heterocyclic 4-membered ring oligomers such as uretdiones. Preferably, the 4-membered or 6-membered ring oligomers of low molecular weight diisocyanates have a functionality within a range from 2 to 6, or preferably within a range from 2.1 to 5.5, or preferably within a range from 2.5 to 5.

Examples of low molecular weight, aliphatic diisocyanates of component C) are hexamethylene diisocyanate (HDI), isophorone diisocyanate (IPDI), butylene diisocyanate (BDI), pentamethylene diisocyanate (PDI), bisisocyanatocyclohexylmethane (HMDI), 2,2,4-trimethylhexamethylene diisocyanate, bisisocyanatomethylcyclohexane, bisisocyanatomethyltricyclodecane, xylene diisocyanate, tetramethylxylylene diisocyanate, norbornane diisocyanate, cyclohexane diisocyanate or diisocyanatododecane, preference being given to hexamethylene diisocyanate (HDI), isophorone diisocyanate (IPDI), butylene diisocyanate (BDI), pentamethylene diisocyanate (PDI), and bis(isocyanatocyclohexyl)methane (HMDI). Particular preference is given to PDI, HDI, IPDI, very particular preference to hexamethylene diisocyanate and pentamethylene diisocyanate.

If aromatic diisocyanates are used as component C), these are preferably toluene 2,4-diisocyanate (2,4-TDI), toluene 2,6-diisocyanate (2,6-TDI) or methylene diphenyl 2,2'-diisocyanate (2,2'-MDI), methylene diphenyl 2,2'-diisocyanate (2,4'-MDI), methylene diphenyl 4,4'-diisocyanate (4,4'-MDI), or mixtures of at least two of these.

The content of isocyanate groups elevated by the use of component C) ensures better foaming since more $CO_2$ is formed in the isocyanate-water reaction.

To accelerate the urethane formation, catalysts can be used in component D). These are typically the compounds known to the person skilled in the art from polyurethane technology. Preference is given here to compounds from the group consisting of catalytically active metal salts, amines, amidines and guanidines. Examples include dibutyltin dilaurate (DBTL), tin acetate, 1,8-diazabicyclo[5.4.0]undecene-7 (DBU), 1,5-diazabicyclo[4.3.0]nonene-5 (DBN), 1,4-diazabicyclo[3.3.0]octene-4 (DBO), N-ethylmorpholine (NEM), triethylenediamine (DABCO), pentamethylguanidine (PMG), tetramethylguanidine (TMG), cyclotetramethylguanidine (TMGC), n-decyltetramethylguanidine (TMGD), n-dodecyltetramethylguanidine (TMGDO), dimethylaminoethyltetramethylguanidine (TMGN), 1,1,4,4,5,5-hexamethylisobiguanidine (HMIB), phenyltetramethylguanidine (TMGP) and hexamethyleneoctamethylbiguanidine (HOB G).

Preference is given to the use of amines, amidines, guanidines or mixtures thereof as catalysts of component D). In addition, preference is also given to the use of 1,8-diazabicyclo[5.4.0]undecene-7 (DBU).

In the process according to the invention, preference is given to dispensing entirely with catalysts.

As component E) it is optionally possible to use salts of weak acids, the corresponding free acids of which have a pKA in water at 25° C. of ≥3.0 and ≤14.0. Examples of suitable salts of weak acids are potassium hydroxide, sodium hydroxide, potassium carbonate, sodium carbonate and sodium hydrogencarbonate, sodium acetate, potassium acetate, sodium citrate, potassium citrate, sodium benzoate, potassium benzoate, also including any desired mixtures of these salts. It is preferable when the salts of weak acids are selected from the group of sodium hydroxide, sodium hydrogencarbonate and sodium carbonate. In this case, the result is a particularly short reaction time.

To improve foam formation, foam stability or the properties of the resulting polyurethane foam, compounds of component F) may be used, where such additives may in principle be any of the anionic, cationic, amphoteric and nonionic surfactants that are known per se, and mixtures of these. Preference is given to using alkyl polyglycosides, EO/PO block copolymers, alkyl or aryl alkoxylates, siloxane alkoxylates, esters of sulfosuccinic acid and/or alkali metal or alkaline earth metal alkanoates or mixtures of at least two of these. Particular preference is given to using EO/PO block copolymers. Preference is given to using solely the EO/PO block copolymers as component F).

In addition, to improve the foam properties of the resulting polyurethane foam, compounds of component G) may be used. These are in principle all the mono- and polyhydric alcohols that are known per se to the person skilled in the art, and mixtures of these. These are mono- or polyhydric alcohols or polyols, such as ethanol, propanol, butanol, decanol, tridecanol, hexadecanol, ethylene glycol, neopentyl glycol, butanediol, hexanediol, decanediol, trimethylolpropane, glycerol, pentaerythritol, monofunctional polyether alcohols and polyester alcohols, polyetherdiols and polyesterdiols or mixtures of at least two of these.

In the preparation of the hydrophilic polyisocyanates H), the ratio of the monofunctional polyalkylene oxides H2) to the low molecular weight diisocyanates H1) is typically adjusted such that, for every 1 mol of OH groups of the monofunctional polyalkylene oxides, there are 1.25 to 20 mol, preferably 2 to 15 mol and more preferably 5 to 13 mol of NCO groups of the low molecular weight diisocyanate H1). This is followed by allophanatization or biuretization and/or isocyanurate formation or uretdione formation. If the polyalkylene oxides H2) are bonded to the preferably aliphatic diisocyanates H1) via urethane groups, allophanatization preferably takes place thereafter. It is further preferable that isocyanate structural units are formed.

A preferred alternative preparation of the hydrophilic polyisocyanates H) is typically effected by reaction of 1 mol of OH groups of the monofunctional polyalkylene oxide component H2) with 1.25 to 20 mol, preferably with 2 to 15 mol and more preferably 5 to 13 mol NCO groups of a polyisocyanate H1) having an isocyanate functionality of 2 to 6, based on aliphatic or aromatic diisocyanates, preferably aliphatic diisocyanates. Examples of such polyisocyanates H1) are biuret structures, isocyanurates or uretdiones based on preferably aliphatic diisocyanates. The polyisocyanate H1) and the polyalkylene oxide H2) are preferably joined to one another via a urethane group or a urea group, preference being given particularly to linkage via urethane groups.

Preference is given to using exclusively aliphatic diisocyanates in the production of polyurethane foams according to the invention. In particular, preference is given to using exclusively aliphatic diisocyanates for components A1), C) and H1).

The reaction can be effected in the presence of urethanization catalysts such as tin compounds, zinc compounds, amines, guanidines or amidines, or in the presence of allophanatization catalysts such as zinc compounds.

The reaction is typically effected at 25° C. to 140° C., preferably at 60° C. to 100° C.

If excess low molecular weight diisocyanate has been employed, the excess of low molecular weight, aliphatic diisocyanate is then removed, preferably by thin-film distillation.

Before, during and/or after the reaction or the distillative removal of the excess diisocyanate, it is possible to add acidic or alkylating stabilizers, such as benzoyl chloride, isophthaloyl chloride, methyl tosylate, chloropropionic acid, HCl or antioxidants such as di-tert-butylcresol or tocopherol.

The NCO content of the hydrophilic polyisocyanates H) is preferably 0.3% to 23% by weight, more preferably 2% to 21% by weight and most preferably 3% to 18% by weight.

Examples of low molecular weight, aliphatic diisocyanates of component H1) are hexamethylene diisocyanate (HDI), isophorone diisocyanate (IPDI), butylene diisocyanate (BDI), pentamethylene diisocyanate (PDI), bisisocyanatocyclohexylmethane (HMDI), 2,2,4-trimethylhexamethylene diisocyanate, bisisocyanatomethylcyclohexane, bisisocyanatomethyltricyclodecane, xylene diisocyanate, tetramethylxylylene diisocyanate, norbornane diisocyanate, cyclohexane diisocyanate or diisocyanatododecane, preference being given to hexamethylene diisocyanate (HDI), isophorone diisocyanate (IPDI), butylene diisocyanate (BDI), pentamethylene diisocyanate (PDI), and bis(isocyanatocyclohexyl)methane (HMDI). Particular preference is given to PDI, HDI, IPDI, very particular preference to hexamethylene diisocyanate and pentamethylene diisocyanate.

If aromatic diisocyanates are used as component H1), these are preferably toluene 2,4-diisocyanate (2,4-TDI), toluene 2,6-diisocyanate (2,6-TDI) or methylene diphenyl 2,2'-diisocyanate (2,2'-MDI), methylene diphenyl 2,2'-diisocyanate (2,4'-MDI), methylene diphenyl 4,4'-diisocyanate (4,4'-MDI), or mixtures of at least two of these.

Examples of higher molecular weight polyisocyanates H2) are polyisocyanates having an isocyanate functionality of 2 to 6 with isocyanurate, urethane, allophanate, biuret, iminooxadiazinetrione, oxadiazinetrione and/or uretdione groups, based on the aliphatic and/or cycloaliphatic diisocyanates mentioned in the paragraph above.

Components H2) used are preferably higher molecular weight compounds with biuret, iminooxadiazinedione, isocyanurate and/or uretdione groups, based on hexamethylene diisocyanate, isophorone diisocyanate and/or 4,4'-diisocyanatodicyclohexylmethane. Preference is further given to isocyanurates. Very particular preference is given to structures based on hexamethylene diisocyanate.

The monofunctional polyalkylene oxides H2) have an OH number of 15 to 250, preferably of 28 to 112, and an ethylene oxide content of 50 to 100 mol %, preferably of 60 to 100 mol %, based on the total amount of the oxyalkylene groups present.

Monofunctional polyalkylene oxides in the context of the invention are understood to mean compounds that have only one isocyanate-reactive group, i.e. one group that can react with an NCO group.

The preparation of polyalkylene oxides H2) by alkoxylation of suitable starter molecules is known from the literature (e.g. Ullmanns Encyclopadie der technischen Chemie [Ullmann's Encyclopedia of Industrial Chemistry], 4th edition, volume 19, Verlag Chemie, Weinheim p. 31-38). Suitable starter molecules are especially saturated monoalcohols such as methanol, ethanol, n-propanol, isopropanol, n-butanol, isobutanol, sec-butanol, diethylene glycol monobutyl ether, and aromatic alcohols such as phenol or monoamines such as diethylamine. Preferred starter molecules are saturated monoalcohols of the aforementioned type. Particular preference is given to using diethylene glycol monobutyl ether or n-butanol as starter molecules.

The monofunctional polyalkylene oxides H2) typically have number-average molecular weights of 220 to 3700 g/mol, preferably of 250 to 2800 g/mol, or preferably of 300 to 2000 g/mol.

The monofunctional polyalkylene oxides H2) preferably have an OH group as isocyanate-reactive group.

Typically, components A) to H) are used in the following amounts:

100 parts by weight of isocyanate-functional prepolymers A)
0.1 to 200 parts by weight of water B)
0 to 30 parts by weight of heterocyclic oligomers C)
0 to 1 part by weight of catalysts D)
0 to 5 parts by weight of salts of weak acids, the corresponding free acids of which have a pKA in water at 25° C. of ≥3.0 and ≤14.0 E)
0 to 10 parts by weight of surfactants F)
0 to 20 parts by weight of alcohols G)
0.5 to 50 parts by weight of hydrophilic polyisocyanate component H)

Preferably, components A) to H) are used in the following amounts:
100 parts by weight of isocyanate-functional prepolymers A)
0.1 to 100 parts by weight of water B)
1 to 20 parts by weight of heterocyclic oligomers C)
0 to 1 part by weight of catalysts D)
0 to 5 parts by weight of salts of weak acids, the corresponding free acids of which have a pKA in water at 25° C. of ≥3.0 and ≤14.0 E)
0 to 5 parts by weight of surfactants F)
0 to 10 parts by weight of alcohols G)
1 to 25 parts by weight of hydrophilic polyisocyanates H)

More preferably, components A) to H) are used in the following amounts:
100 parts by weight of isocyanate-functional prepolymers A)
1 to 60 parts by weight of water B)
2 to 15 parts by weight of heterocyclic oligomers C)
0 to 0.5 part by weight of catalysts D)
0 part by weight of salts of weak acids, the corresponding free acids of which have a pKA in water at 25° C. of ≥3.0 and ≤14.0 E)
0 to 3 parts by weight of surfactants F)
0 part by weight of alcohols G)
2 to 15 parts by weight of hydrophilic polyisocyanates H)

In a preferred embodiment of the process according to the invention, component A) has a proportion by weight of low molecular weight diisocyanates having a molar mass of 140 to 278 g/mol of below 1.0% by weight, preferably of below 0.5% by weight, preferably of below 0.3% by weight, or preferably of below 0.1% by weight, based on the prepolymer. The proportion by weight of low molecular weight diisocyanates is preferably adjusted via distillation.

In a preferred embodiment of the process according to the invention aliphatic isocyanates are used as component A1).

In a preferred embodiment of the process according to the invention, at least the following steps are conducted:
I) preparing the prepolymer A) from components A1), A2) and optionally A3), D),
II) optionally mixing components A), C) and H) and other isocyanate-containing components to obtain a prepolymer mixture,
III) optionally adding A3) and optionally D),
IV) optionally mixing component B) with all other components, especially D), E), F) and G), apart from the prepolymer mixture,
V) mixing the prepolymer mixture obtained in I) to III) with the mixture from IV).

Preferably, the temperature in at least one of steps I) to IV) is chosen within a range from 2 to 70° C., or preferably within a range from 10 to 50° C., or preferably from 20 to 40° C.

Preferably, the mixture, after step IV), is applied to a substrate and allowed to cure. The curing is preferably conducted at a temperature within a range from 20 to 50° C. With the aid of convection ovens or infrared dryers, the curing and simultaneous drying can also be conducted in higher temperature ranges, for example between 50 and 200° C.

The polyurethane foams according to the invention are preferably produced by mixing components A), produced from components A1), A2) and optionally A3), D), optionally with C) and/or H), in any sequence, and then with a mixture of B) and optionally D), E), F), G), foaming the mixture and curing, preferably by chemical crosslinking. Preferably, components A), C) and H) are pre-mixed with one another. Any salts E) to be used and any surfactants F) are preferably added to the reaction mixture in the form of their aqueous solutions.

The foaming can in principle be effected by means of the carbon dioxide formed in the reaction of the isocyanate groups with water, but the use of other blowing agents is likewise possible. For instance, it is also possible in principle to use blowing agents from the class of the hydrocarbons such as $C_3$-$C_6$-alkanes, e.g. butanes, n-pentane, iso-pentane, cyclo-pentane, hexanes or the like or halogenated hydrocarbons such as dichloromethane, dichloromonofluoromethane, chlorodifluoroethanes, 1,1-dichloro-2,2,2-trifluoroethane, 2,2-dichloro-2-fluoroethane, especially chlorine-free hydrofluorocarbons such as difluoromethane, trifluoromethane, difluoroethane, 1,1,1,2-tetrafluoroethane, tetrafluoroethane (R 134 or R 134a), 1,1,1,3,3-pentafluoropropane (R 245 fa), 1,1,1,3,3,3-hexafluoropropane (R 256), 1,1,1,3,3-pentafluorobutane (R 365 mfc), heptafluoropropane or else sulfur hexafluoride. Mixtures of these blowing agents are also usable.

The subsequent curing is typically effected at room temperature.

In a preferred embodiment of the process according to the invention, the ethylene oxide content of A2 is ≥50% by weight, or preferably ≥55% by weight, or preferably ≥60% by weight.

In a preferred embodiment of the process according to the invention, the mixture of the isocyanate-containing components has a molar ratio of urethane groups to isocyanate groups within a range from 1.0 to 5.0, or preferably within a range of 1.1-4.0, or preferably within a range from 1.2 to 3.

In a preferred embodiment of the process according to the invention, there is a molar ratio of NCO groups to OH groups in the reaction of components A1) to A3) to give the isocyanate-functional prepolymer A) of <5, or preferably of <4, or preferably of <3, or preferably within a range from 1 to 5, or preferably within a range from 1.5 to 4.5.

In a preferred embodiment of the process according to the invention, the isocyanate-functional prepolymer A has a viscosity of ≤50 000 mPas, preferably of ≤25000, or preferably of ≤10 000, or preferably within a range from 100 to 20000 mPas.

In a preferred embodiment of the process according to the invention, at least a portion of the isocyanate-containing components has an isocyanate functionality of >2, preferably within a range from 2 to 6, or preferably within a range from 2.1 to 5.

In a preferred embodiment of the process according to the invention, the polyalkylene oxide A2) has an OH number within a range from 40 to 450 mg KOH/g, preferably within a range from 75 to 400, or preferably within a range from 113 to 300.

Moreover, the present invention further provides the polyurethane foams produced by the process according to the invention, and for the use of the hydrophilic, aliphatic polyurethane foams as a constituent of a wound dressing, a cosmetic article or an incontinence product.

As already described above, the polyurethane foams according to the invention are preferably produced by mixing components A), produced from components A1), A2) and optionally A3), D), optionally with C) and/or H), in any sequence, and then with a mixture of B) and optionally D), E), F), G), foaming the mixture and curing, preferably by chemical crosslinking. Preferably, components A), C) and H) are pre-mixed with one another. Any salts E) to be used and any surfactants F) are preferably added to the reaction mixture in the form of their aqueous solutions. Preferably, the polyurethane foams according to the invention are hydrophilic and have aliphatic units.

The polyurethane foams according to the invention or the polyurethane foams produced in accordance with the invention preferably have a porous, at least partly open-cell structure with cells in communication with one another. The density of the polyurethane foams is preferably 50 to 300 g/l.

The absorption capacity for physiological saline in the polyurethane foams is preferably 300% to 4000%, or preferably from 800% to 3500%, or preferably from 1000% to 3000%, based on the dry weight of the foam. The measurement is effected by the following method: (determination to DIN EN 13726-1, Part 3.2).

By comparison with other hydrophilic foams, the polyurethane foams according to the invention, even without the use of superabsorbent polymers, can achieve very high absorption of physiological saline. It will be appreciated that the incorporation of superabsorbents is also possible in the case of the polyurethane foams according to the invention. The same techniques of incorporation of superabsorbents into the polyurethane foams according to the invention can be employed here as in EP 3235520 for the polyurethane foams described therein.

The polyurethane foams have good mechanical strength and high elasticity. Typically, tensile strength values are greater than 40 kPa, elongation at break values greater than 30% with a density in the range from 50 to 300 g/l (determination in each case by the standards as described later under Methods).

After the production, the polyurethane foams can be processed by methods known per se to give two-dimensional materials which can then be used, for example, as a constituent of a wound dressing, of a cosmetic article or of an incontinence product. In general, for this purpose, slabstock foams are cut to the desired thickness by standard methods, which to obtain two-dimensional materials having a thickness of typically from 10 µm to 5 cm, preferably from 0.1 mm to 1 cm, more preferably from 0.1 mm to 6 mm, most preferably from 0.2 mm to 6 mm.

With the aid of suitable casting techniques, the two-dimensional materials described can alternatively be obtained directly by application and foaming of the composition according to the invention to a substrate, for example an optionally pretreated paper, a film, a nonwoven or a textile.

In a preferred variant, for this purpose, a mixture of the starting materials as described in the PCT application numbered WO 2011/006608 is applied to a substrate by means of a coating bar, and then the foaming follows after the coating. The gap height of the coating bar is generally in the range from 0.2 to 20 mm, preferably from 0.5 to 5 mm and most preferably from 0.8 to 2 mm. The film width of the coating bar to be used can be matched to the particular end use. Examples are film widths between 10 and 5000 mm, preferably between 20 and 2000 mm.

Preference is given to a casting method in which, while the polyurethane foam is being cast to a layer or a substrate, a further layer is applied to the top side of the polyurethane foam, preferably before the polyurethane foam has dried. Such a process is described in the patent application with application number EP 17156493.3 and can likewise be employed here.

The polyurethane foams generally contain only a small water-extractable proportion of not more than 2% by weight, preferably of not more than 1% by weight, meaning that they contain only very small amounts of chemically unbound constituents.

Moreover, the polyurethane foams may be bonded, laminated or coated with further materials, for example based on hydrogels, (semi-)permeable films, foam films, coatings, hydrocolloids or other foams.

The polyurethane foams according to the invention are particularly suitable for production of wound dressings. The polyurethane foams here may be in direct or indirect contact with the wound. However, preference is given to using the polyurethane foams in direct contact with the wound in order to assure, for example, optimal absorption of wound fluid.

The polyurethane foams that are used as wound dressing must additionally be sterilized in a further process step. For sterilization, the processes known per se to the person skilled in the art are used, in which sterilization is effected by thermal treatment, chemical substances such as ethylene oxide, or irradiation, for example by gamma irradiation. The irradiation can optionally be effected under protective gas atmosphere. The polyurethane foams according to the invention have the great advantage that they are not discoloured on irradiation, especially on irradiation with gamma rays.

Likewise possible is addition, incorporation or coating of or with antimicrobial, pharmaceutical or biological active ingredients or other additives that have a positive effect, for example in relation to wound healing and the avoidance of microbial contamination.

The invention further provides a polyurethane prepolymer mixture comprising the following components:
A) a polyurethane prepolymer obtainable from
   A1) low molecular weight diisocyanates of molar mass from 140 to 278 g/mol with
   A2) polyalkylene oxides having an OH functionality of two or more, preferably within a range from 2 to 6, or preferably within a range from 2.1 to 5,
   A3) optionally further isocyanate-reactive components not covered by A2);
C) optionally heterocyclic 4-membered or 6-membered ring oligomers of low molecular weight diisocyanates having a molar mass of 140 to 278 g/mol, preferably having an isocyanate functionality of 2 to 6, or an isocyanate functionality of 2.1 to 5;
D) optionally catalysts;
H) optionally hydrophilic polyisocyanates obtainable by reaction of
   H1) low molecular weight diisocyanates of molar mass from 140 to 278 g/mol and/or polyisocyanates preparable therefrom and having an isocyanate functionality of 2 to 6, or an isocyanate functionality of 2.1 to 5;
   H2) monofunctional polyalkylene oxides of OH number from 10 to 250, or preferably of 20 to 200, and of ethylene oxide content from 50 to 100 mol %, based on the total amount of the oxyalkylene groups present, wherein the polyurethane prepolymer mixture, especially components A, C and H, have an isocyanate content within a range from 2% to 8% by weight, or preferably within a range from 3% to 7%, or preferably within a range from 4% to 6.5% by weight, and a content of urethane groups within a range from 1.0 to 3.5 mol/kg, or preferably within a range from 1.5 to 3.0 mol/kg, or preferably within a range from 1.7 to 2.8 mol/kg, based in each case on the total amount of the polyurethane prepolymer mixture.

The polyurethane prepolymer mixture according to the invention is preferably converted to the polyurethane foam as in the above-described process for producing a polyurethane foam. All the components mentioned for the polyurethane prepolymer mixture have the same properties as already described for these components in connection with the process according to the invention.

The invention further relates to the use of the polyurethane prepolymer mixture according to the invention or of the polyurethane foam according to the invention for production of a wound dressing, a cosmetic article or an incontinence product.

Preferably, the polyurethane foam used for the production of the wound dressing, the cosmetic article or the incontinence product has at least three of the following properties:
a) a quotient of breaking strength and F20 of at least 3.5, preferably of at least 4, or preferably of at least 5, or preferably within a range from 3.5 to 30, or preferably within a range from 4 to 30, or preferably within a range from 5 to 30, or preferably within a range from 7.5 to 25;
b) a liquid absorption of ≥300%, or preferably of ≥500%, or preferably of ≥1000%, or preferably within a range from 300 to 3000%, or preferably within a range from 400 to 2500%;
c) a density within a range from 50 to 300 g/l, or preferably within a range from 60 to 200 g/l;
d) a breaking strength of at least 50 kPa, or preferably of at least 100, or preferably of at least 120; or preferably within a range from 50 to 500, or preferably within a range from 100 to 400;
e) an F20 of at most 50 kPa, or preferably of at most 45 kPa, or preferably of at most 40 kPa, or preferably of at most 20 kPa; or preferably within a range from 1 to 50 kPa, or preferably within a range from 2 to 40 kPa, or preferably within a range from 2 to 20 kPa.

Preferably, the polyurethane foam has the combination of features a)+b)+c) or a)+b)+d) or a)+b)+e) or a)+c)+d) or a)+c)+e) or a)+d)+e) or b)+c)+d) or b)+c)+e) or c)+d)+e) or a)+b)+c)+d), or a)+b)+c)+e) or a)+c)+d)+e) or a)+b)+c)+d)+e).

The invention further relates to a polyurethane foam having at least the following properties:
a) a quotient of breaking strength and F20 of at least 3.5 is, preferably of at least 4, or preferably of at least 5, or preferably within a range from 3.5 to 30, or preferably within a range from 4 to 29, or preferably within a range from 5 to 28, or preferably within a range from 7.5 to 25;
b) a liquid absorption of ≥300%, or preferably of ≥500%, or preferably of ≥1000%, or preferably within a range from 300 to 3000%, or preferably within a range from 400 to 2500%;
c) a density within a range from 50 and 300 g/l, or preferably within a range from 60 to 200 g/l;

d) a breaking strength of at least 50 kPa, or preferably of at least 100, or preferably of at least 120; or preferably within a range from 50 to 500, or preferably within a range from 100 to 400;
e) an F20 of at most 50 kPa, or preferably of at most 45 kPa, or preferably of at most 40 kPa, or preferably of at most 20 kPa; or preferably within a range from 1 to 100 kPa, or preferably within a range from 2 to 40 kPa, or preferably within a range from 2 to 20 kPa.

The invention further relates to a wound dressing, to a cosmetic article or to an incontinence product obtainable using polyurethane foams according to the invention, or polyurethane foams produced in accordance with the invention.

Methods

Unless indicated otherwise, all percentages are based on weight.

Viscosity was determined at 23° C. according to DIN 53019.

NCO contents were determined by volumetric means according to DIN-EN ISO 11909.

Liquid absorption was determined according to DIN EN 13726-1:2002. Liquid absorbed is reported in % of the dry weight of the foam, where the dry weight of the foam corresponds to 100%, as follows:

Liquid absorption in % =

$$100 \cdot \frac{\text{Mass after absorption} - \text{mass before absorption (dry weight)}}{\text{mass before absorption}}$$

The reported values for breaking strength, elongation at break and stress at 20% elongation (also referred to as F20) were determined according to DIN EN ISO 527-2. Breaking strength is the force per unit area of the specimen that has to be expended to cause breakage, i.e. rupture, of the specimen material under the conditions of the standard. Elongation at break indicates the elongation of the specimen material shortly before breakage based on the original length of the specimen. 20% elongation or F20 indicates how much force per unit area of the specimen has to be expended in the extension of the specimen material to extend the specimen by 20% of its original length.

Substances and Abbreviations Used:

Desmodur® N 3300: aliphatic polyisocyanate (HDI isocyanurate), NCO content 21.8%, Covestro AG, Leverkusen, Germany.

Baymedix® FP520: hydrophilized aliphatic polyisocyanate (hydrophilized HDI isocyanurate), NCO content 17.4%, (urethane content 0.4 mol/kg), Covestro AG, Leverkusen, Germany Determination of Urethane Content For the present invention, the urethane content can be calculated from the stoichiometry of the urethane-forming reaction between hydroxyl groups and isocyanate groups. Since the hydroxyl groups are fully converted to urethane groups in all examples, the following formula can be used for calculation:

$$\text{Urethane content} = \frac{\% \text{ by wt. of hydroxyl component} \cdot \text{OHN}}{5610 \frac{\text{kg}}{\text{mol}}}$$

where OHN denotes hydroxyl number of the hydroxyl component used or the corresponding average value for multiple components. Examples of possible hydroxyl components are mono- or polyfunctional alcohols or polyols. Specific examples are described under A1), A3), G) or H2).

In the case of subsequent removal of urethane-free components from the product mixture, for example by a distillation process, there is an increase in the polyol content and hence also in the urethane content of the product mixture.

Calculation Example on the Basis of Example 4

Urethane content before distillation:

$$\text{Urethane content} = \frac{63.71 \cdot 190}{5610 \frac{\text{kg}}{\text{mol}}} = 2.16 \frac{\text{mol}}{\text{kg}}$$

Urethane content after distillation:

$$\text{Urethane content} = \frac{70.07 \cdot 190}{5610 \frac{\text{kg}}{\text{mol}}} = 2.37 \frac{\text{mol}}{\text{kg}}$$

It will be apparent to the person skilled in the art that the formula utilized here has to be modified or extended when, for example, reactants that already contain urethane groups are used, other urethane-forming reactions are used or competing reactions can occur (for example urea formation in the presence of amines).

Thickness Measurement:

The measurement of layer thickness was ascertained with a compressed air gauge connected to a display from Heidehain (MT25P) to display the layer thickness.

Density Measurement:

To determine the density, a piece of sample was punched out with the aid of a punch in dimensions of 5×5 cm² (with rounded corners and a curve radius of 3 mm). The height was ascertained from the average of a 5-fold determination by means of the method described above.

For subsequent calculation of the density, the mass of the piece of sample was determined using a Mettler Toledo XS603S balance.

EXAMPLES

Example 1 (Inventive)

To a mixture of 1680 g of HDI and 5.0 g of dibutyl phosphate were added dropwise at 80° C., within 30 min, 2960 g of a polyalkylene oxide having a molar mass of 591 g/mol (OH number 190 mg KOH/g), started from 1,3-propylene glycol, and a proportion by weight of ethylene oxide of 87%, and stirring of the mixture was continued until an NCO content of 9.1% had been attained (3.5 h). The excess HDI was removed by thin-film distillation at 140° C. and 0.7 mbar. The mixture had an NCO content of 5.0% and a viscosity of 5140 mPas. The calculated urethane content is 2.4 mol/kg.

Example 2 (Inventive)

To a mixture of 662 g of HDI and 1.8 g of dibutyl phosphate were added dropwise, at 80° C. within 30 min, 1167 g of a polyalkylene oxide having a molar mass of 591 g/mol (OH number 190 mg KOH/g), started from 1,3- propylene glycol, and a proportion by weight of ethylene oxide of 87%, and stirring of the mixture was continued until an NCO content of 9.1% had been attained (3.5 h). The excess HDI was removed by thin-film distillation at 140° C. and 0.4 mbar. A prepolymer having an NCO content of 5.0% and a viscosity of 4500 mPas was obtained. The calculated urethane content is 2.4 mol/kg. Subsequently, 5% Desmodur N 3300 was added. The mixture had an NCO content of 5.7% and a viscosity of 3700 mPas. The calculated urethane content is 2.3 mol/kg.

Example 3 (Inventive)

To a mixture of 531 g of HDI and 1.6 g of dibutyl phosphate were added dropwise, at 80° C. within 30 min, 1169 g of a polyalkylene oxide having a molar mass of 591 g/mol (OH number 190 mg KOH/g), started from 1,3-propylene glycol, and a proportion by weight of ethylene oxide of 87%, and stirring of the mixture was continued until an NCO content of 5.8% had been attained (3.5 h). The excess HDI was removed by thin-film distillation at 140° C. and 0.6 mbar. A prepolymer having an NCO content of 3.7% and a viscosity of 11500 mPas was obtained. The calculated urethane content is 2.4 mol/kg. Subsequently, 5% Baymedix® FP520 was added. The mixture had an NCO content of 4.1% and a viscosity of 15700 mPas. The calculated urethane content is 2.3 mol/kg.

Example 4 (Inventive)

To a mixture of 541 g of HDI and 1.5 g of dibutyl phosphate were added dropwise, at 80° C. within 30 min, 1059 g of a polyalkylene oxide having a molar mass of 591 g/mol (OH number 190 mg KOH/g), started from 1,3-propylene glycol, and a proportion by weight of ethylene oxide of 87%, and stirring of the mixture was continued until an NCO content of 7.3% had been attained (3.5 h). The excess HDI was removed by thin-film distillation at 140° C. and 0.6 mbar.
A prepolymer having an NCO content of 4.5% and a viscosity of 6690 mPas was obtained. The calculated urethane content is 2.4 mol/kg. Subsequently, 5% Baymedix® FP520 was added. The mixture had an NCO content of 4.7% and a viscosity of 9800 mPas. The calculated urethane content is 2.3 mol/kg.

Example 5 (Inventive)

To a mixture of 662 g of HDI and 1.8 g of dibutyl phosphate were added dropwise, at 80° C. within 30 min, 1167 g of a polyalkylene oxide having a molar mass of 591 g/mol (OH number 190 mg KOH/g), started from 1,3-propylene glycol, and a proportion by weight of ethylene oxide of 87%, and stirring of the mixture was continued until an NCO content of 9.1% had been attained (3.5 h). The excess HDI was removed by thin-film distillation at 140° C. and 0.4 mbar. A prepolymer having an NCO content of 5.0% and a viscosity of 4500 mPas was obtained. The calculated urethane content is 2.4 mol/kg. Subsequently, 5% Baymedix® FP520 was added. The mixture had an NCO content of 5.2% and a viscosity of 7030 mPas. The calculated urethane content is 2.3 mol/kg.

Example 6 (Inventive)

To a mixture of 4616 g of HDI and 12 g of dibutyl phosphate were added dropwise, at 80° C. within 30 min, 7384 g of a polyalkylene oxide having a molar mass of 591 g/mol (OH number 190 mg KOH/g), started from 1,3-propylene glycol, and a proportion by weight of ethylene oxide of 87%, and stirring of the mixture was continued until an NCO content of 10.4% had been attained (3.5 h). The excess HDI was removed by thin-film distillation at 140° C. and 0.3 mbar. A prepolymer having an NCO content of 5.5% and a viscosity of 3450 mPas was obtained. The calculated urethane content is 2.4 mol/kg. Subsequently, 5% Baymedix® FP520 was added. The mixture had an NCO content of 5.9% and a viscosity of 4100 mPas. The calculated urethane content is 2.3 mol/kg.

Example 7 (Inventive)

To a mixture of 4984 g of HDI and 12 g of dibutyl phosphate were added dropwise, at 80° C. within 30 min, 7016 g of a polyalkylene oxide having a molar mass of 591 g/mol (OH number 190 mg KOH/g), started from 1,3-propylene glycol, and a proportion by weight of ethylene oxide of 87%, and stirring of the mixture was continued until an NCO content of 12.5% had been attained (3.5 h). The excess HDI was removed by thin-film distillation at 140° C. and 0.3 mbar. A prepolymer having an NCO content of 5.7% and a viscosity of 2670 mPas was obtained. The calculated urethane content is 2.3 mol/kg. Subsequently, 5% Baymedix® FP520 was added. The mixture had an NCO content of 6.1% and a viscosity of 3220 mPas. The calculated urethane content is 2.2 mol/kg.

Example 8 (Inventive)

To a mixture of 420 g of HDI and 1.6 g of dibutyl phosphate were added dropwise, at 80° C. within 30 min, 1021 g of a polyalkylene oxide having a molar mass of 591 g/mol (OH number 190 mg KOH/g), started from 1,3-propylene glycol, and a proportion by weight of ethylene oxide of 87%, and stirring of the mixture was continued until an NCO content of 23.5% had been attained (3.5 h). The excess HDI was removed by thin-film distillation at 140° C. and 0.4 mbar. A prepolymer having an NCO content of 7.5% and a viscosity of 905 mPas was obtained. The calculated urethane content is 2.2 mol/kg. Subsequently, 5% Baymedix® FP520 was added. The mixture had an NCO content of 8.0% and a viscosity of 1440 mPas. The calculated urethane content is 2.2 mol/kg.

Example 9 (Inventive)

To a mixture of 710 g of HDI and 0.5 g of dibutyl phosphate were added dropwise, at 80° C. within 30 min, 200 g of polyethylene glycol having a molar mass of 400 g/mol (OH number 281 mg KOH/g), and stirring of the mixture was continued until an NCO content of 7.5% had been attained (3.5 h). The excess HDI was removed by thin-film distillation at 140° C. and 0.4 mbar. A prepolymer having an NCO content of 5.0% and a viscosity of 15 900 mPas was obtained. The calculated urethane content is 3.2 mol/kg. Subsequently, 5.0% Baymedix® FP520 was added. The mixture had an NCO content of 5.1% and a viscosity of 23 100 mPas. The calculated urethane content is 3.0 mol/kg.

Example 10 (Inventive)

To a mixture of 361 g of HDI and 2.1 g of dibutyl phosphate were added dropwise, at 80° C. within 30 min, 1216 g of a polyalkylene oxide having a molar mass of 998 g/mol (OH number 112 mg KOH/g), started from 1,3-propylene glycol, and a proportion by weight of ethylene oxide of 89%, and stirring of the mixture was continued until an NCO content of 15.8% had been attained (3.5 h). The excess HDI was removed by thin-film distillation at 140° C. and 0.4 mbar. A prepolymer having an NCO content of 4.9% and a viscosity of 1360 mPas was obtained. The calculated urethane content is 1.5 mol/kg. Subsequently, 5.0% Baymedix® FP520 was added. The mixture had an NCO content of 5.5% and a viscosity of 2020 mPas. The calculated urethane content is 1.5 mol/kg.

Example 11 (Non-Inventive)

To a mixture of 1260 g of HDI and 2.0 g of dibutyl phosphate were added dropwise, at 80° C. within 30 min, 1972 g of a polyalkylene oxide having a molar mass of 3951 g/mol (OH number 28.4 mg KOH/g), started from 1,3-propylene glycol, and a proportion by weight of ethylene oxide of 78%, and stirring of the mixture was continued until an NCO content of 18.1% had been attained (3.5 h). The excess HDI was removed by thin-film distillation at 140° C. and 0.5 mbar. A prepolymer having an NCO content of 2.0% and a viscosity of 3690 mPas was obtained. The calculated urethane content is 0.5 mol/kg. Subsequently, 5.0% Baymedix® FP520 was added. The mixture had an NCO content of 2.6% and a viscosity of 4250 mPas. The calculated urethane content is 0.5 mol/kg.

Example 12 (Non-Inventive)

The isocyanate-containing mixtures from Examples 10 and 11 were mixed in a ratio of 1:1. The mixture had an NCO content of 4.3% and a viscosity of 2940 mPas. The calculated urethane content is 0.97 mol/kg.

Example 13 (Non-Inventive)

To a mixture of 1130 g of HDI and 1.78 g of dibutyl phosphate were added dropwise, at 80° C. within 30 min, 652 g of tetraethylene glycol (OH number 580 mg KOH/g), and stirring of the mixture was continued until an NCO content of 15.7% had been attained (3.5 h). The calculated urethane content is 3.8 mol/kg. During cooling to room temperature, there was crystallization to form a white solid. Owing to the solid character, it was not possible to process the material to give the foam.

Example 14 (Non-Inventive)

To a mixture of 998 g of HDI and 1.9 g of dibutyl phosphate were added dropwise, at 80° C. within 30 min, 873 g of tetraethylene glycol (OH number 580 mg KOH/g), and stirring of the mixture was continued until an NCO content of 6.4% had been attained (7 h). The calculated urethane content is 4.8 mol/kg. During cooling to room temperature, there was crystallization to form a white solid. Owing to the solid character, it was not possible to process the material to give the foam.

Example 15 (Non-Inventive)

To a mixture of 1184 g of HDI and 2.58 g of dibutyl phosphate were added dropwise, at 80° C. within 2 h, 1395 g of a polyalkylene oxide having a molar mass of 4680 g/mol (OH number 36 mg KOH/g), started from glycerol, a proportion by weight of ethylene oxide of 72% and a proportion by weight of propylene oxide of 28%, and stirring of the mixture was continued until an NCO content of 21.4% had been attained (2.5 h). The excess HDI was removed by thin-film distillation at 140° C. and 0.1 mbar. A prepolymer having an NCO content of 2.5% and a viscosity of 3500 mPas was obtained. The calculated urethane content is 0.6 mol/kg.

Example 16 (Non-Inventive)

To a mixture of 2805 g of HDI and 3.25 g of dibutyl phosphate were added dropwise, at 80° C. within 30 min, 649 g of a polyalkylene oxide having a molar mass of 591 g/mol (OH number 190 mg KOH/g), started from 1,3-propylene glycol, and a proportion by weight of ethylene oxide of 87%, and stirring of the mixture was continued until an NCO content of 37.6% had been attained (1 h). The excess HDI was removed by thin-film distillation at 140° C. and 0.5 mbar. A prepolymer having an NCO content of 9.1% and a viscosity of 700 mPas was obtained. The calculated urethane content is 2.2 mol/kg. Subsequently, 5.0% Desmodur N 3300 was added. The mixture has an NCO content of 9.3% and the calculated urethane content is 2.1 mol/kg.

Production of Foams from the Examples

The prepolymer mixtures from the examples were each introduced into a 500 ml PP cup from Sarstedt and homogenized by means of a stirrer from Pendraulik (Disperlux green 037) at a speed of 930 rpm for 15 seconds. Subsequently, a defined amount (Table 1) was added. The water phase consisted of 93.5% water, 1.3% sodium hydrogencarbonate, 0.4% citric acid monohydrate and 4.8% Pluronic PE6800. Then the mixture was stirred for a further 7 seconds. The mixture was applied with the aid of a coating bar (gap height 1500 μm) to a release paper from Felix Schoeller (Y05200). After 60 seconds (based on the start of the experiment), a needled release paper from Felix Schoeller (Y05200) was applied. The resultant foam was left to stand at room temperature for drying overnight.

TABLE 1

Properties of foams produced from the examples

| Example | NCO content of the isocyanate-containing mixture [%]* | Urethane content [mol/kg] | Mass ratio of the isocyanate-containing mixture* to aqueous phase | Foam thickness [mm] | Density [g/l] | Breaking strength [kPa] | Elongation at break [%] | F20 [kPa] | Breaking strength/ F20 | Absorption [%] | Swelling (length expansion) [%] |
|---|---|---|---|---|---|---|---|---|---|---|---|
| 1 | 5.0 | 2.4 | 5:1 | 5.5 | 113 | 339 | 515 | 46.0 | 7.4 | 1818 | 30.8 |
| 2 | 5.7 | 2.3 | 7:1 | 5.0 | 88 | 147 | 437 | 9.3 | 15.8 | 1762 | 25.0 |
| 3 | 4.1 | 2.3 | 5:1 | 5.7 | 120 | 170 | 456 | 14.1 | 12.1 | 1462 | 26.0 |
| 4 | 4.7 | 2.3 | 5:1 | 5.5 | 106 | 167 | 577 | 11.7 | 14.3 | 1751 | 23.4 |
| 5 | 5.2 | 2.3 | 5:1 | 6.0 | 96 | 131 | 476 | 9.8 | 13.4 | 1824 | 21.4 |

TABLE 1-continued

Properties of foams produced from the examples

| Example | NCO content of the isocyanate-containing mixture [%]* | Urethane content [mol/kg] | Mass ratio of the isocyanate-containing mixture* to aqueous phase | Foam thickness [mm] | Density [g/l] | Breaking strength [kPa] | Elongation at break [%] | F20 [kPa] | Breaking strength/ F20 | Absorption [%] | Swelling (length expansion) [%] |
|---|---|---|---|---|---|---|---|---|---|---|---|
| 6 | 5.9 | 2.3 | 5:1 | 7.3 | 85 | 92 | 338 | 12.9 | 7.1 | 1382 | 22.3 |
| 7 | 6.1 | 2.2 | 5:1 | 7.1 | 76 | 134 | 288 | 22.6 | 5.9 | 922 | 21.3 |
| 8 | 8.0 | 2.2 | 4:1 | 15.8 | 61 | 68 | 165 | 17.2 | 4.0 | 738 | 19.9 |
| 9 | 5.1 | 3.0 | 5:1 | 8.0 | 89 | 140 | 277 | 21.6 | 6.5 | 858 | 15.0 |
| 10 | 5.5 | 1.5 | 7:1 | 10.7 | 85 | 106 | 458 | 8.7 | 12.2 | 2600 | 36.8 |
| 11 | 2.6 | 0.5 | 5:1 | 1.5 | 492 | 519 | 564 | 78.0 | 6.7 | 961 | 74.5 |
| 12 | 4.3 | 0.97 | 5:1 | 1.6 | 401 | 495 | 475 | 67.6 | 7.3 | 866 | 59.8 |
| 13** | 15.7 | 3.8 | n.d. | n.d. | n.d. | n.d. | n.d. | n.d. | n.d. | n.d. | n.d. |
| 14** | 6.4 | 4.8 | n.d. | n.d. | n.d. | n.d. | n.d. | n.d. | n.d. | n.d. | n.d. |
| 15 | 2.5 | 0.6 | 5:1 | 1.9 | 316 | 155 | 46 | 80.0 | 1.9 | 724 | 52.5 |
| 16 | 5.3 | 0.8 | 5:1 | 7.4 | 123 | 83 | 124 | 17.0 | 4.9 | 1800 | 44.4 |
| 17 | 9.3 | 2.1 | 5:1 | 13.4 | 57 | 34 | 59 | 18.7 | 1.8 | 445 | 12.4 |

*the isocyanate-containing mixture is based on the sum total of all isocyanate-containing components, especially components A), C) and H)
**Examples 13 and 14 were not processible to give a foam owing to their solid character.

As already mentioned in the introduction to the application, it is desirable to provide a foam suitable, for example, for production of a wound dressing having optimized properties. These optimized properties include maximum flexibility coupled with high elongation at break and maximum absorption capacity. It can be seen from the values in Table 1 that the F20 values of the inventive examples are all below 50 kPa with a quotient of breaking strength and the F20 values of greater than 3.5. By contrast, the non-inventive examples do not have such a combination in any case and are therefore much less flexible and/or insufficiently tear-resistant and hence unsuitable for use as wound dressing. Moreover, it was easily possible to use the isocyanate-containing examples according to the invention to produce foams within the desired density range from 50 to 300 g/l, especially within the preferred range from 60 to 200 g/l.

The invention claimed is:

1. A process for producing polyurethane foams, in which compositions comprising
   A) isocyanate-functional prepolymers obtainable by the reaction of
      A1) low molecular weight diisocyanates of molar mass from 140 to 278 g/mol with
      A2) polyalkylene oxides having an OH functionality of two or more,
      A3) optionally further isocyanate-reactive components not covered by A2);
   B) water in an amount of at least 2% by weight, based on the total weight of the composition;
   C) optionally heterocyclic 4-membered or 6-membered ring oligomers of low molecular weight diisocyanates having a molar mass of 140 to 278 g/mol,
   D) optionally catalysts;
   E) optionally salts of weak acids, the corresponding free acids of which have a pKA in water at 25° C. of ≥3.0 and ≤14.0;
   F) optionally surfactants; and
   G) optionally mono- or polyhydric alcohols or polyols;
   H) optionally hydrophilic polyisocyanates obtainable by reaction of
      H1) low molecular weight diisocyanates of molar mass from 140 to 278 g/mol and/or polyisocyanates preparable therefrom and having an isocyanate functionality of 2 to 6 with
      H2) monofunctional polyalkylene oxides of OH number from 10 to 250 and of ethylene oxide content from 50 to 100 mol %, based on the total amount of the oxyalkylene groups present,
   are provided, foamed and cured,
   wherein the isocyanate-containing components have a total isocyanate content within a range from 2% to 8% by weight and a content of urethane groups of 1.0 to 3.5 mol/kg, based in each case on the total amount of the isocyanate-containing components, and
   wherein the polyurethane foam has an F20 value (F20 corresponds to the tension at 20% elongation in the stress strain test according to DIN EN ISO 527-2) of ≤50 kPa and a quotient of break strength determined according to DIN EN ISO 527-2 to F20 of at least 3.5.

2. The process according to claim 1, characterized in that component A) has a proportion by weight of low molecular weight diisocyanates having a molar mass of 140 to 278 g/mol of below 1.0% by weight, based on the prepolymer.

3. The process according to claim 1, characterized in that aliphatic isocyanates are used as component A1).

4. The process according to claim 1, characterized in that the following steps are conducted:
   I) preparing the prepolymer A) from components A1), A2) and optionally A3), D),
   II) optionally mixing components A), C) and H) and other isocyanate-containing components to obtain a prepolymer mixture,
   III) optionally adding A3) and optionally D),
   IV) optionally mixing component B) with all other components, apart from the prepolymer mixture,
   V) optionally mixing the prepolymer mixture obtained in I) to III) with the mixture from IV).

5. The process according to claim 1, characterized in that the ethylene oxide content of A2) is ≥50% by weight.

6. The process according to claim 1, characterized in that the mixture of isocyanate-containing components has a molar ratio of urethane groups to isocyanate groups of 1.0 to 5.0.

7. The process according to claim 1, characterized in that there is a molar ratio of NCO to OH groups in the reaction of components A1) to A3) to give the isocyanate-functional prepolymer A) of ≤5.

8. The process according to claim 1, characterized in that the isocyanate-functional prepolymer A has a viscosity of ≤50000 mPas.

9. The process according to claim 1, characterized in that at least some of the isocyanate-containing components have an isocyanate functionality of >2.

10. The process according to claim 1, characterized in that the polyalkylene oxide A2) has an OH number within a range from 40 to 450 mg KOH/g.

11. A polyurethane foam obtainable by a process according to claim 1.

12. A wound dressing, a cosmetic article or an incontinence product obtainable using polyurethane foams according to claim 11.

13. The process according to claim 1, wherein the polyurethane foam further has at least the following properties:
   b) a liquid absorption determined according to DIN EN 13726-1:2002≥300%;
   c) a density between 50 and 300 g/l;
   d) a breaking strength determined according to DIN EN ISO 527-2 of at least 50 kPa.

\* \* \* \* \*